United States Patent [19]

Smith et al.

[11] Patent Number: 4,533,632

[45] Date of Patent: Aug. 6, 1985

[54] PRODUCTION OF A CEPHALOSPORIN BY FERMENTATION

[75] Inventors: Alan Smith, Ulverston; Peter J. Bailey, Sparkbridge, both of England

[73] Assignee: Glaxo Group Limited, London, England

[21] Appl. No.: 406,039

[22] Filed: Aug. 6, 1982

Related U.S. Application Data

[63] Continuation of Ser. No. 171,929, Jul. 18, 1980, abandoned.

[30] Foreign Application Priority Data

Jul. 19, 1979 [GB] United Kingdom ................. 7925283

[51] Int. Cl.$^3$ .................... C12P 35/00; C12P 35/06
[52] U.S. Cl. ......................................... 435/47; 435/49
[58] Field of Search ........................................ 435/47

[56] References Cited

U.S. PATENT DOCUMENTS 3,912,589  10/1975  Smith ................................... 435/47
3,926,728  12/1975  Kanzaki et al. ....................... 435/51

OTHER PUBLICATIONS

Konecny et al., J. of Antibiotics XXVI, No. 3, pp. 135–141 (1973).
Movita et al., Phil. Trans. R. Soc. Lond. B289, pp. 181–190 (1980).
Fujisawa et al., Ag. Biol. Chem. 39(6), pp. 1295–1301 (1975).
Fujisawa et al., Agr. Biol. Chem. 39(6), pp. 1303–1309 (1975).

*Primary Examiner*—Alvin E. Tanenholtz
*Attorney, Agent, or Firm*—Bernard, Rothwell & Brown

[57] ABSTRACT

A process for greatly improving the yields of cephalosporin nucleus produced by fermentation is described. Cephalosporin C-producing microorganisms are fermented in the presence of an acetylesterase enzyme so that cephalosporin C formed is immediately converted into desacetyl cephalosporin C before any non-enzymic degradation occurs. Fermentation to produce desacetyl cephalosporin C enables yield increases of cephalosporin nucleus of about 40% to be realized, and greater increases are possible if the fermentation is extended. The preferred cephalosporin C-producing organism is *Acremonium chrysogenum*, and mutants thereof that are capable of producing esterases in situ. Alternatively, esterases obtained from a variety of other sources may be added or formed in situ, for example from a strain of *Rhodosporidium*.

9 Claims, No Drawings

PRODUCTION OF A CEPHALOSPORIN BY FERMENTATION

This is a continuation of application Ser. No. 171,929, filed July 18, 1980 and now abandoned.

This invention relates to the production of a cephalosporin by fermentation.

Cephalosporin C fermentations are a primary source of cephalosporin nucleus that is used in quantity for the preparation of a large number of semi-synthetic cephalosporin antibiotics. Such fermentations generally take place for a period of several days and it has been observed that because cephalosporin C itself in aqueous solution is subject to non-enzymic decomposition by $\beta$-lactam hydrolysis, a typical industrial fermentation results in a loss of about 25% of the observed cephalosporin C titre due to non-enzymic decomposition.

It has also been generally observed that about 15% of the cephalosporin nucleus produced during fermentation is present as desacetyl cephalosporin C. Although this compound is also useful as a source of cephalosporin nucleus, it is generally inconvenient and uneconomic to attempt to isolate the amount of desacetyl cephalosporin C formed in view of the differences in techniques that are needed and the scale of the operation. Thus, the 15% of the cephalosporin nucleus that occurs as desacetyl cephalosporin C also represents a loss and so generally a total of about 40% of the cephalosporin nucleus that is produced is not available for extraction as cephalosporin C.

We have now surprisingly discovered that, contrary to that which was previously supposed by earlier workers (Konecny et al., J. Antib., Vol. XXVI, No. 3, p. 140), desacetyl cephalosporin C is much more stable with respect to non-enzymic $\beta$-lactam degradation than cephalosporin C in culture broth. We have unexpectedly failed to detect any decomposition of desacetyl cephalosporin C in aqueous solutions and culture broths under fermentation conditions even with sensitive assay methods.

We have used this discovery to develop a process for the conversion of cephalosporin C into desacetyl cephalosporin C during fermentation as soon as it is formed. Such a process gains in two ways. Firstly there is practically no loss of cephalosporin product due to decomposition because of the surprising stability of desacetyl cephalosporin C, and secondly the desacetyl cephalosporin C that is produced in normal fermentations may also be recovered. We have thus found that large increases in recovery of cephalosporin product can be obtained. The increase is typically about 40% but this may vary depending on the desacetyl cephalosporin C content of the normal cephalosporin C fermentation and on the kinetics of cephalosporin C accumulation.

Furthermore, we have also found that desacetyl cephalosporin C continues to accumulate if the fermentation is continued for periods much longer than those normally used for cephalosporin C production. Generally speaking, the accumulation of cephalosporin C begins to fall off after about six days fermentation, which is the standard period, but we have found that up to as much as a further 50% of utilisable cephalosporin nucleus may be obtained if the fermentation time in the presence of the acetylesterase is prolonged by, for example, 2 days or about a third of the time. Thus, if the fermentation is prolonged, the total gain in utilisable cephalosporin nucleus obtained by deliberately producing desacetyl cephalosporin C can be as much as 90% more than that produced in a normal cephalosporin C fermentation.

It will be realised, therefore that these are very considerable increases in yield of utilisable cephalosporin nucleus that are of considerable economic value. Furthermore, the limitations that are imposed by the instability of cephalosporin C on the development and yields of cephalosporin nucleus production by fermentation may be greatly reduced.

Desacetyl cephalosporin C may readily be converted to pharmacologically valuable derivatives such as cephalothin and cephaloridine.

According to the invention, therefore, we provide a process for the preparation of desacetyl cephalosporin C which comprises fermenting a cephalosporin C-producing microorganism in the presence of an amount of an acetylesterase enzyme effective to convert substantially all the cephalosporin C produced into desacetyl cephalosporin C before non-enzymic degradation of the cephalosporin C occurs.

The acetylesterase may either be added right at the start of the fermentation, or at the start of the cephalosporin C accretion phase and optionally at intervals during the fermentation. Alternatively, the acetylesterase may be developed throughout the fermentation process in situ.

The esterase enzyme may be derived from an extremely wide range of sources. Thus the esterase may be derived from inter alia, higher plants, bacteria, yeasts and fungi. Suitable higher plant sources include the peel of citrus fruits, as described in British Patent Specification No. 966,222, and wheat germ as described in our British Patent Specification No. 1,121,308. The latter Specification also describes suitable acetylesterase activity in the bacterial genus Rhizobium. Suitable yeast sources include yeasts of the genus Rhodotorula as described for example in our British Patent Specification No. 1,474,519. Microorganisms of the class *Basidiomycetes*, as described in our British Patent Specification No. 1,531,212 and bacteria of the species *B. subtilis* as described in App. Microbiol. Vol. 30, No. 3, p. 413 are also suitable sources. A source of the enzyme which we have found particularly suitable is the microbial genus Rhodosporidium, especially the species *Rhodosporidium toruloides*, for example strain CBS 349, as described in our above-mentioned British Patent Specification No. 1,531,212.

A suitable screening procedure to determine useful sources of esterase may be found in our British Patent Specification No. 1,531,121. Although the description of the procedure in this document refers generally to determining esterase levels produced by microorganisms of the class *Basidiomycetes* the procedure may be readily adapted to screen for esterases produced by other sources by a suitable choice of conditions.

The process of the invention will desirably be carried out by culturing a known cephalosporin C-producing strain in the presence of the acetylesterase enzyme under aerobic conditions, preferably in submerged culture, with shaking or stirring with air or oxygen. The fermentation medium employed should contain an assimilable source of carbon, a digestible source of nitrogen and, if desired, growth-promoting substances as well as inorganic salts.

Suitable carbon sources include, for example, glucose, sucrose, starch, soluble starch, n-paraffins, vegetable and animal oils, acetic acid, methanol, glycerol, sorbitol and ethanol.

Suitable nitrogen sources include, for example, natural nitrogen-containing substances or materials produced from them, such as meat extracts, peptone, casein, cornsteep liquor, yeast extracts, soya bean flour, tryptone, cotton seed meal and wheat bran. Nitrogen-containing organic or inorganic compounds may also be used, for example, urea, nitrates and ammonium salts such as ammonium acetate, ammonium chloride, ammonium sulphate and ammonium phosphate.

Inorganic salts which may be used in the fermentation medium may be, for example, sulphates, nitrates, chlorides, carbonates and phosphates of potassium, magnesium and calcium.

Growth-promoting substances which may be used include, for example, cysteine, cystine, thiosulphate, methyl oleate and, in particular, methionine and also trace elements such as iron, zinc, copper and manganese.

Culturing conditions such as temperature, pH and fermentation time, are selected such that the strain employed may accumulate a maximum amount of the desired cephalosporin. For example, the fermentation is advantageously carried out at a temperature ranging from 15°–45° C., preferably about 25° C., at a pH of from 4–9, e.g. from 5–8 and preferably about 6, and for from 1–20 days, preferably 4–10 days.

The most preferred cephalosporin C-producing strain is a strain of *Acremonium chrysogenum* (formerly known as *Cephalosporium acremonium*). Some mutants of *Acremonium chrysogenum* have also been found capable of generating large quantities of acetylesterase *in situ* throughout the fermentation. Other microorganisms of the genus Cephalosporium, for example strains of *Cephalosporium polyaleurum*, and some microorganisms of the genus Emericellopsis and Streptomyces, for example strains of *Emericellopsis glabra*, *Emericellopsis microspora* and *Streptomyces lactamdurans* are also capable of producing cephalosporin C.

The amount of esterase or esterase-containing material required to convert cephalosporin C formed in the fermentation into desacetyl cephalosporin C may be simply assessed by preliminary assays of enzyme activity or small-scale trial runs, and will depend on the esterase and on the reaction conditions employed. The course of the reaction may conveniently be followed by HPLC or by separating the product by thin-layer or paper chromatography using an appropriate support-/solvent system combination and assaying densitometrically. Suitable methods are described in our British Patent Specification No. 1,531,212 referred to above. Generally speaking, it will be convenient to employ a substantial excess of esterase.

The method used to isolate the desacetyl cephalosporin C product will in general employ conventional techniques, for example as described in British Patent Specification No. 1,433,528. Following centrifugation or filtration of the fermentation broth e.g. through a bed of kieselguhr, isolation may be effected, for example, by desalting the solution by adsorption onto carbon followed by elution with acetone and water. The eluate may be further purified by absorption onto an anion-exchange resin (for example Amberlite IRA-68 in the acetate form), eluting the desacetyl cephalosporin from the resin with potassium acetate solution and precipitating the product with acetone.

In general, the esterase will be in a form that can be readily distributed in the fermentation broth to hydrolyse the cephalosporin C. Thus where the esterase comes from another microorganism, a sample of the whole culture or of the separated cells may be employed, preferably after treatment to render the cells non-viable, and, if desired, after rupture of the cells, for example by conventional methods such as ultrasonic treatment, treatment with lytic enzymes of treatment with detergents. Other preparations of cells, which permit their storage with retention of the esterase activity may also be used, for example acetone dried powders or acetone treated cells.

The microbial esterase may also be employed in cell-free form. Thus a filtrate or supernatant obtained from the culture may be employed. If desired, the cells may be ruptured, for example as described above, before filtration or centrifugation. Alternatively, the cell free esterase may be further purified by conventional means. The techniques which may be used include precipitation of the enzyme e.g. with salts or with organic solvents, such as acetone, chromatography e.g. on ion-exchange resins or on supports with a special affinity for the enzyme, and desalting e.g. gel filtration or dialysis. The cell-free esterase may be used as a solution, as a precipitate or as a suitably immobilised preparation.

Where the esterase comes from a higher plant it is desirable to use an enzyme-containing extract of the plant. Such an extract may be prepared by conventional methods, which will in general involve initial release of the enzyme from the plant by physical techniques, such as grinding or pressing as described in British Patent Specificaion No. 966,222, or by chemical techniques, for example by treatment of the plant with a hydrocarbon solvent such as petroleum ether, as described in British Patent Specification No. 1,121,308. The resulting preparation, either with or without removal of cell debris may be added directly to the hydrolysis solution. Alternatively, if desired, the preparation may be treated further, for example using the techniques described above for microbial enzymes, to obtain a cell-free esterase which may be used as described for the microbial enzyme.

It is clear that in using the above-described forms of the acetylesterase, the enzyme will actually be added to the fermentation broth. In an alternative procedure, however, it is also possible to generate the enzyme in situ by use of a mixed culture of the cephalosporin-producing organism with one of the esterase producing organisms mentioned earlier. Alternatively microorganisms, for example mutants of *Acremonium chrysogenum*, which produce high levels of esterase in addition to cephalosporin C throughout the fermentation may also be used. Such microorganisms have not previously been reported and are a further feature of the invention.

Such mutants of *Acremonium chrysogenum* may be produced by a variety of methods including those outlined in Techniques for the Development of Micro-Organisms by H. I. Adler in "Radiation and Radioisotopes for Industrial Microorganisms", Proceedings of the Symposium, Vienna, 1973, p. 241, International Atomic Energy Authority. These methods include (i) Ionising radiation, for example X- and $\gamma$-rays, uv light, uv light in the presence of a photosensitizing agent, for example 8-methoxypsoralen; nitrous oxide; hydroxylamine; pyrimidine base analogues e.g. 5-bromouracil; acridines; alkylating agents e.g. ethyl methane sulphonate or mustard gas; hydrogen peroxide; phenols; formaldehyde; heat: and (ii) genetic techniques, such as recombination, transduction, transformation, lysogenisation, lysogenic conversion and selective techniques for spontaneous mutants.

We have found the use of uv light to be suitable.

The existence of a mutant according to this aspect of the invention may be ascertained by suitable screening procedures. Thus, in a first procedure, mutants which produce substantial levels of DAC and very little cephalosporin C throughout the course of the fermentation are identified by standard assay procedures. In a second procedure, mutants which will effect the deacetylation of added cephalosporin C are also identified by standard assay procedures. Mutants according to this aspect of the invention are those which will satisfy both screening procedures.

The invention will now be more particularly described in the following non-limiting Examples. All temperatures are in °C.

Strain IMI 237183 was deposited at the Commonwealth Mycological Institute, Kew, England on Apr. 9, 1979.

Strains of this type are described, inter alia, in 'Cephalosporium-artige Schimmelpilze (Hyphomycetes)' by Walter Gams (Verlag, W. Germany) 1971, pp 109–111.

EXAMPLE 1

(a) Preparation of acetylesterase

*Rhodosporidium toruloides* CBS 349 was grown in 2 l flasks on a liquid medium comprising glucose (2%), yeast extract (1%), peptone (1%), potassium dihydrogen phosphate (0.5%) and polypropylene glycol (0.1%) for 72 hr. A 100 ml suspension of the yeast was transferred to a sterile flask and cooled to 4°. To this was added acetone (30 ml) which had been previously cooled to −10°. After a short period of stirring further volumes of cold acetone were added sequentially to raise the acetone concentration stepwise to 75% v/v. The yeast cells were allowed to settle out, the supernatant decanted and fresh neat acetone added. After thoroughly mixing, the excess acetone was decanted and the treated cells washed twice by centrifugation in sterile water. The washed cells were resuspended in sterile water to yield a suspension with an esterase activity of 3.5 iu/ml.

(b) Fermentation of desacetylcephalosporin C (DAC)

The fermentation was carried out in shake flasks containing medium (9.5 ml) of the composition given below to which 0.4 ml of the esterase suspension prepared in (a) was given post autoclave:

| Corn steep liquor | 0.5% as nitrogen |
| --- | --- |
| Lactose | 46 g/l |
| Glucose | 2 g/l |
| Methionine | 2.3 g/l |
| Phenylacetylethanolamine | 1.5 g/l |
| Calcium carbonate | 16 g/l |
| Urea | 0.8 g/l |
| Ammonium sulphate | 3.4 g/l |
| Maize oil | 6 drops per flask |
| (pH(adjusted pre autoclave with NaOH) | 6.6 |

The flasks were inoculated with *A. chrysogenum* strain IMI 237183 (0.5 ml) which had been previously grown for 48 hours in a medium containing corn steep liquor (0.1% as nitrogen), ammonium acetate (5.5 g/l), sucrose (25 g/l) and calcium carbonate (10 g/l). The flask was incubated at 25° on a shaker for 5 days and the DAC titre was determined by HPLC. Table 1 shows the titre of DAC after 3, 4 and 5 days; each figure represents the mean of three individually assayed flasks. Control flasks containing medium and microorganism but no esterase were run at the same time.

TABLE 1

| Time (days) | DAC ($\mu$g/ml) Esterase present | DAC ($\mu$g/ml) No esterase |
| --- | --- | --- |
| 3 | 352 | 89 |
| 4 | 1732 | 137 |
| 5 | 2615 | 478 |

EXAMPLE 2

Inoculum Development

A freeze dried ampoule of *A. chrysogenum* IMI 237183 was reconstituted by adding liquid Sabouraud's medium (2 ml). The resulting cell suspension was used to inoculate a 250 ml flat-sided bottle (Blake bottle) containing solidified Sabouraud's medium. The culture was incubated for 14 days at 25°.

| Sabouraud's medium | |
| --- | --- |
| Maltose | 4.0% w/v |
| Malt extract | 2.4% |
| Peptone | 1.0% |
| Agar | 2.5% |
| Water to | 100% pH adjusted to 7.5 prior to sterilisation. |

Approximately 50 ml of sterile water and glass beads were added after completion of the incubation to wash off the surface culture. The suspended cells were then used to inoculate a 500 ml flat-sided bottle (Roux bottle) containing solidified Sabouraud's medium. About 4 ml of suspension was used for each Roux bottle which was then incubated for 12 days at 25°.

A cell suspension was prepared by washing off the surface culture with 40 ml of sterile water and glass beads. This suspension was used to inoculate the liquid seed stages in 2 l. baffled flat-bottomed flasks containing 600 ml peptone/malt extract medium.

| Peptone/malt extract medium | |
| --- | --- |
| Peptone | 1.0% w/v |
| Malt extract | 2.4% |
| Yeatex granules | 2.68% |
| Chalk | 0.5% |
| Soya bean oil | 1.96% |
| Water to | 100% pH adjusted to 7.5 prior to sterilisation. |

The liquid seed stages were each inoculated with 6 ml cell suspension from the Roux bottle and then incubated at 25° on a shaker at 110 rev/min. with a 4.9 cm throw for 72 hours. Two liquid seed stage cultures were bulked to provide inoculum for the main fermentation stage.

Two fermentations were carried out each in a 7 liter fermenter with stirring at 25° using the fermentation medium of Example 1 (b) except that maize oil was present at 3.0% v/v. The pH was controlled at 6.0±0.1 using 1M sulphuric acid and 8M ammonium hydroxide. A dissolved oxygen tension greater than 30% saturation was maintained throughout the fermentation. An auxiliary feed of 24% ammonium sulphate solution was applied for part of the fermentation to maintain the free ammonia level at greater than 500 ppm. When the batched carbon supplies were exhausted at about 72 hours, a feed of glucose was applied for the remainder of the fermentation to maintain the respiration rate. This amounted to approximately 15 ml/hr. of 55% cerelose (glucose monohydrate).

In order to demonstrate the advantage of a fermentation producing desacetyl cephalosporin C (DAC) acetylesterase from *Rhodosporidium toruloides* CBS 349 (prepared as in Example 1a) was added to one of the fermentation at the beginning of the cephalosporin accretion phase (48 hr). An amount equivalent to 400 ml of yeast broth was added.

The fermentations ran for 8 days and samples were assayed daily for cephalosporin C and DAC using an HPLC assay.

A comparison between the control fermentation producing cephalosporin C and the esterase treated fermentation producing DAC is shown in Table 3.

TABLE 3

| Time | Control | | Esterase treated | |
| --- | --- | --- | --- | --- |
| h. | Ceph C µg/g | DAC µg/g | Ceph C µg/g | DAC µg/g |
| 45 | 400 | 50 | 500 | 0 |
| 69 | 1,800 | 120 | 200 | 1,500 |
| 93 | 1,800 | 160 | 0 | 2,200 |
| 117 | 2,700 | 320 | 0 | 3,000 |
| 141 | 2,500 | 430 | 0 | 3,300 |
| 165 | 2,600 | 610 | 0 | 3,500 |
| 189 | 2,300 | 720 | 0 | 3,900 |

Table 4 hours DAC titres at 141 and 189 h expressed as Cephalosporin C equivalents.

| Time h. | Control Ceph C (µg/g) | Esterase treated DAC (in Ceph C equiv.) | % increase in Yield for DAC |
| --- | --- | --- | --- |
| 141 | 2,500 | 3,663 | 47% |
| 189 | 2,300 | 4,329 | 88% |

We claim:

1. A process for the preparation of desacetyl cephalosporin C which comprises fermenting a cephalosporin C-producing microorganism in the presence of an amount of an acetylesterase enzyme effective to convert substantially all the cephalosporin C produced into desacetyl cephalosporin C before non-enzymic degradation of the cephalosporin C occurs.

2. The process of claim 1 wherein fermentation is carried out at from 15°–45° C. at a pH of from 4 to 9 for from 1 to 20 days.

3. The process of claim 1 wherein the cephalosporin C-producing microorganism is a strain of the species *Acremonium chrysogenum*.

4. The process of claim 1 wherein an excess of the acetylesterase enzyme is added before accretion of the cephalosporin C.

5. The process of claim 1 wherein the acetylesterase is derived from the bacterial genus Rhizobium, the yeast genus Rhodotorula or from the class Basidiomycetes, or species *B. subtilis*.

6. The process of claim 1 wherein the acetylesterase is derived from *Rhodosporidium toruloides* strain CBS 349.

7. The process of claim 1 in which the esterase is used in the form of a cell-free preparation.

8. The process of claim 1 wherein the acetylesterase is generated in situ by fermentation of the esterase-producing microorganism.

9. The process of claim 3 wherein the acetylesterase is generated in situ by the cephalosporin C-producing microorganism during the fermentation.

* * * * *